United States Patent [19]

Knesel, Jr. et al.

[11] Patent Number: 4,962,044
[45] Date of Patent: Oct. 9, 1990

[54] TEST TUBE FILTER/DISPENSER APPARATUS AND METHOD

[75] Inventors: Ernest A. Knesel, Jr., Greensboro; Daniel R. Shoemaker, Elon College; David V. Fansler, Graham, all of N.C.

[73] Assignee: Hoffmann-La Roche Inc., Nutley, N.J.

[21] Appl. No.: 185,655

[22] Filed: Apr. 25, 1988

[51] Int. Cl.⁵ .................. B01D 33/00; B01D 37/00
[52] U.S. Cl. .................. 436/177; 422/101; 436/178; 436/180; 210/359; 210/515
[58] Field of Search .............. 422/101; 436/178, 177, 436/180; 210/515, 359

[56] References Cited

U.S. PATENT DOCUMENTS

| | | |
|---|---|---|
| 688,544 | 12/1901 | Pitts . |
| 847,722 | 3/1907 | Bender . |
| 3,481,477 | 12/1969 | Farr . |
| 4,065,383 | 12/1977 | Skare et al. .................. 210/27 |
| 4,189,385 | 2/1980 | Greenspan .................. 210/136 |
| 4,210,623 | 7/1980 | Breno et al. .................. 422/101 |
| 4,643,981 | 2/1987 | Card .................. 436/500 |

FOREIGN PATENT DOCUMENTS 2130604 3/1972 France .

Primary Examiner—Barry S. Richman
Assistant Examiner—Janelle D. Waack
Attorney, Agent, or Firm—George M. Gould; William H. Epstein; John J. Schlager

[57] ABSTRACT

According to the invention, a piston fit filter/dispenser vial and method of using same is provided. The vial comprises a conventional filter, for example a piston fit serum filter closing the lower end of the vial and a closure having a pressure source fitting closing off the upper end of the vial. The vial also includes a transfer tube having a first end inside the vial adjacent to the filter and a second end outside vial. Filtrate, for example filtered blood serum, within the vial may be transferred in predetermined aliquots to one or more awaiting sample containers from the vial by applying a predetermined volume of air from a pressure source via the pressure source fitting whereby displaced serum is forced up the transfer tube and out of the vial.

15 Claims, 1 Drawing Sheet

TEST TUBE FILTER/DISPENSER APPARATUS AND METHOD

FIELD OF THE INVENTION

The invention relates to a test tube filter/dispenser apparatus and method, which is especially suitable for filtering and dispensing measured aliquots of blood serum derived from a whole blood sample.

BACKGROUND

In the examination of blood samples, it is often necessary or desirable to examine blood serum after it has been separated from the suspended cellular material, and for this purpose it is customary to subject the specimen tubes, in which the blood samples are delivered to the laboratory, to centrifuging action to cause the settling of the cells to the bottom of the specimen tube. Since many laboratories process large numbers of blood samples every day, facility of handling specimens and the ease of drawing off and retaining serum specimens are important to successful and safe operation.

The most widely employed method of separating the liquid phase component from the solid phase components of a blood mixture is centrifugation. When the serum is to be subjected to a diagnostic analysis with, for example, an automated electronic analyzer, it is important to employ a particulate-free specimen. Fibrin fibers are often the cause of analyzer malfunctions when they clog conduits or orifices in the analyzer.

Filtration has been employed previously to remove solid particles such as minute fibers of fibrin not readily separated by centrifugation. Illustrative of the prior art blood component filtration devices are those described in U.S. Pat. Nos. 3,481,477; 3,512,940; 3,693,804 and 3,832,141. In these serum separators, the sample is collected in a test tube and an elongated sampling tube is provided to fit within the test tube. In the lower end of the sampling tube is a piston head which makes a sliding seal with the side walls of the test tube. A filter is mounted in a passageway extending through the piston head to the interior of the sampling tube. As the sampling tube and piston head are pushed into the test tube, fluid will pass through the filter into the interior of the sampling tube leaving the residue in the bottom of the test tube. The sampling tube may subsequently be withdrawn at which time the filtrate which will be serum, will be withdrawn with the sampling tube.

Filtered serum may be withdrawn from the sampling tube for an automated blood analysis by using, for example, an aspirating tube. See, for example, U.S. Pat. No. 4,602,995. Alternatively, aliquots of serum may be transferred from the sampling tube into one or more sample containers by pipetting.

For automated laboratory analysis of blood samples, it is desirable to separate each sample into multiple pre-measured aliquots of serum. In this manner, a plurality of separate blood samples may be aliquoted and then all sample aliquots requiring a particular laboratory analysis may be run through an automatic analyzer sequentially.

There is a disadvantage associated with transferring serum from the sampling tube using pipetting or aspiration in that each of these techniques requires the introduction of a foreign object into the serum, sometimes more than once. For example, each introduction of a pipette or aspirating tube into serum sample involves the risk of contaminating the sample and also presents problems in maintaining the sterility of the pipette and/or aspirating tube.

SUMMARY OF THE INVENTION

The invention relates to an apparatus and method for collecting filtrate—particularly filtered serum—from a whole blood sample and transferring predetermined aliquots of the filtrate to one or more separate containers. More particularly, the invention relates to improvements in piston filter-type vials for serum filtration.

According to the invention, a piston fit filter/dispenser vial is provided. The vial has a hollow shaft comprising a side wall defining an interior, the hollow shaft having an upper end and an lower end. A piston fit filter means is located in the lower end of the hollow shaft. The filter means closes the lower end of the hollow shaft. Additionally, a transfer tube is provided having a first end located within the interior of the hollow shaft and a second end located outside the hollow shaft for transferring serum from within the shaft to a point outside. Finally, the vial includes a closure means located in the upper end of the hollow shaft for closing the hollow shaft. The closure means includes a fitting for receiving an external air pressure source. When the external air pressure source is engaged with the closure and air pressure is applied, filtrate within the vial is transferred therefrom via the transfer tube.

The invention also comprises a method for filtering and dispensing a filtrate such as serum using the piston fit filter-dispenser vial described above. According to the inventive method, the vial is inserted into a test tube containing a sample to be filtered, such as a centrifuged whole blood sample. As the vial is pushed down into the test tube, the sample is filtered and resulting filtrate passes through the filter and is collected within the hollow shaft of the vial. Following this operation, predetermined volumes of air may be forced into the vial from an external air pressure source via the fitting in the closure located in the upper end of the hollow shaft of the vial. This in turn causes a predetermined quantity of filtrate to be forced through the transfer tube and out of the vial.

DESCRIPTION OF THE DRAWINGS

The preferred embodiment of the invention will now be described with reference to the following drawings, which are merely exemplary and are not meant to limit the scope of the invention in any respects.

DESCRIPTION OF THE PREFERRED EMBODIMENT

Figure 1A:
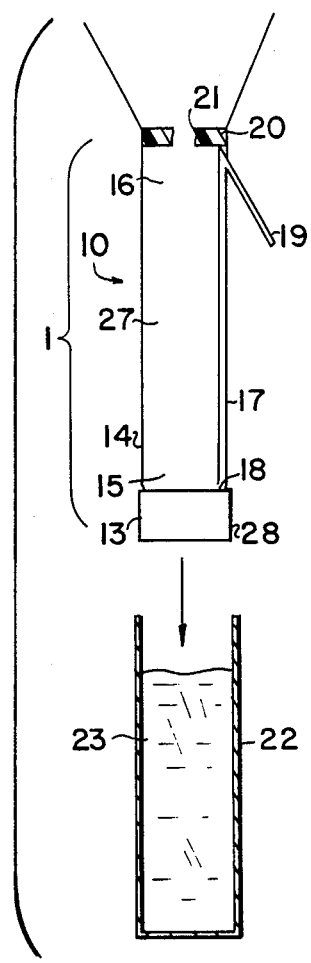
FIGS. 1a-1c show a first embodiment of the piston fit filter/dispenser vial according to the invention in cross-section.
Figure 1B:
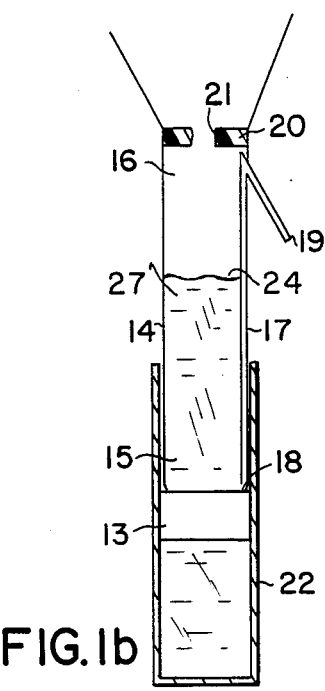
Figure 1C:
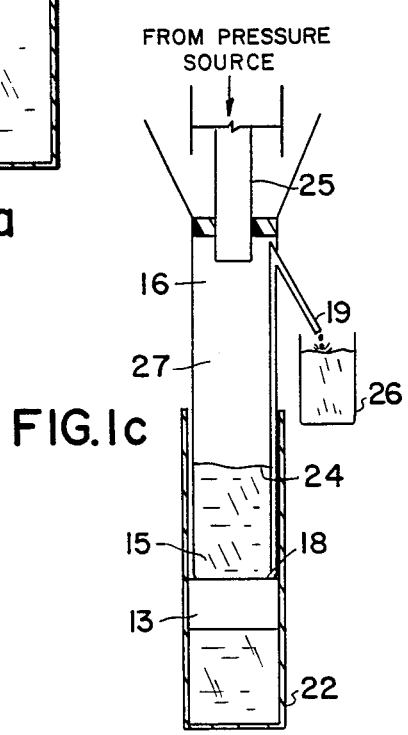

FIGS. 1a-1c illustrate a first embodiment of the piston fit filter/dispenser vial according to the invention. FIGS. 1a-1c illustrate from left to right the vial 1 prior to insertion into a test tube 22 filled with a whole blood sample 23 to be filtered (FIG. 1a); vial 1 after insertion into the test tube 22 but before aliquoting has occurred (FIG. 1b); and vial 1 after insertion into test tube 22 and during application of air pressure via the pressure source 25 to aliquote a fraction of filtered serum 24 into a container 26 (FIG. 1c).

Referring to FIG. 1a, the vial comprises a hollow shaft 10 having a side wall 14 defining an interior 27. The hollow shaft 10 has a lower end 15 which is closed by filter assembly 28. The hollow shaft 10 also has an upper end 16 which is closed by closure 20.

A transfer tube 17 is partially located within the hollow shaft 10. The transfer tube 17 has a first end 18 which opens into the interior 27 of the hollow shaft 10 preferably adjacent to the filter assembly 28 in the lower end 15. The transfer tube 17 has a second end 19 which is located outside the hollow shaft 10.

As shown in FIGS. 1a-1c, the transfer tube 17 extends out through the side wall 14 of the hollow shaft 10.

The transfer tube 17 may be constructed integrally with the side wall 14 as shown or may be constructed as a separate element (not illustrated).

The vial and transfer tube are preferably manufactured from a transparent or semi-transparent material. The vial may, for example, be constructed of glass or plastic which is preferably non-porous and inert to the intended filtrate. Suitable plastic materials for a serum filter application would include, polyacrylate, polyvinyl and polystyrene.

The filter element 28 includes a filter 13. It will be understood that the invention does not reside in the particular configuration of the filter assembly 28 and any suitable filter assembly as is known in the art may be employed.

The filter may be constructed of any suitable conventional material. However, in the case where the vial is to be used for filtering blood serum, the filter material should preferably be inert to blood. The filter material should have pores which permit the passage of soluble blood components but prevent passage of insoluble blood components through the filter. More particularly, the pores should be sized to deny passage of solid and semi-solid particulate material having a spherical diameter of greater than 50 microns.

Suitable filter materials would include porous plastic materials, more particularly porous polyethylene, porous polyurethane, porous tetrafluoroethylene and the like, porous ceramic materials, scintered glass, glass wool, and the like may also be employed.

The closure 20 includes a pressure source fitting 21, which is sized to receive the external pressure source 25 as shown in FIG. 1c.

No particular material of construction is preferred for the closure 20. The closure 20 may be constructed integrally with the side wall 14 or may be constructed as a separate element which is held in the upper end 16 of the hollow shaft 10 by friction fit, for example.

Figure 2:
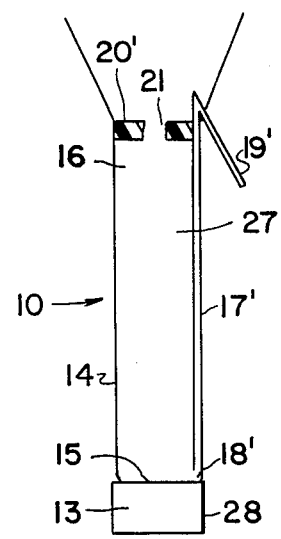
FIG. 2 shows a second embodiment of the piston fit filter/dispenser vial according to the invention in cross-section.

An alternative embodiment is illustrated in FIG. 2 wherein the transfer tube 17 extends out through closure 20 instead of through side wall 14.

The operation of the vial according to the invention will now be described with reference to FIGS. 1a-1c. The following description of the operation of the vial according to the invention will, for illustrative purposes, relate to the filtration of serum from whole blood. However, it is understood that the vial according to the invention may be used to filter other substances besides whole blood.

In a method according to the invention, a whole blood sample 23 is introduced into test tube 22. Following centrifugation to separate out the heavier components in the blood, the vial 1 is pushed down into the test tube 22. See FIG. 1b. The pressure source fitting 21 permits air within the vial 1 to escape as serum 24 fills up inside.

As shown in FIG. 1b, the vial after being pushed into est tube 22 filters out serum 24, which is then collected in the interior 27 of the hollow shaft 10. At this stage, and as shown in FIG. 1c, the external pressure source 25, for example a conventional automatic pipette, may be inserted into pressure source fitting 21. A predetermined volume of air may be forced into the interior 27 of the vial.

As shown in FIG. 1c the air introduced into the vial displaces a predetermined aliquot of filtered serum 24, which flows through transfer tube 17 out into container 26. This aliquoting operation may be repeated as many times as necessary to fill one or more additional containers 26 with predetermined aliquots of filtered serum 24 from the whole blood sample 23.

The predetermined aliquots of filtered serum 24 within individual containers 26 are then ready to be transferred to automated analyzing equipment, for example.

It will be recognized from the foregoing description that one advantage provided by the vial and method according to the invention is the elimination of the need to employ a seperate pipetting operation to transfer filtered serum from the interior 27 of the vial 1 to awaiting containers 26. The vial 1 thus serves a dual function as not only a filter apparatus but also a dispensing apparatus. The external pressure source 25 will not need to come in contact with the filtered serum 24. This enhances cleanliness and efficiency in laboratories which may be handling large numbers of whole blood samples for analysis.

While certain specific embodiments of the filter/dispenser vial and method of use according to the invention have been described in the foregoing description, it will be understood that various modifications within the spirit and scope of the invention may occur to those skilled in the art. Therefore, it is intended that no limitations be placed on the invention except as defined by the scope of the following claims.

I claim:

1. A piston-type filter/dispenser vial for dispensing measured aliquots of filtrate upon the application of air pressure to said vial from an external air pressure source, said vial comprising:
   a. an elongated hollow shaft for the collection of liquid including a side wall defining an interior, said hollow shaft having an upper end and a lower end;
   b. a piston fit filter means located in and closing the said lower end of the hollow shaft, said filter means providing a sealing and sliding contact with the inside surface of a test tube and said filter means allowing flow of filtrate from a test tube into said hollow shaft when said hollow shaft is inserted filter end first into a test tube;
   c. a transfer tube means for the transport of liquid from the interior of the hollow shaft to outside the hollow shaft, under pressure from an external pressure source which does not come into direct physical contact with said filtrate, having a first end located within the interior of the hollow shaft and a second end located outside the hollow shaft; and
   d. closure means located in the upper end of the hollow shaft for closing the hollow shaft, said closure means including a fitting for receiving an external air pressure source during transport of liquid from the interior of the hollow shaft to the outside thereof.

2. The vial of claim 1, wherein the first end of the transfer tube means is located adjacent to said filter means in the lower end of the hollow shaft.

3. The vial of claim 1, wherein the transfer tube extends out through the side wall of the hollow shaft.

4. The vial of claim 3, wherein the first end of the transfer tube is located adjacent to said filter means in the lower end of the hollow shaft.

5. The vial of claim 1, wherein the transfer tube means extends out through the closure means.

6. The vial of claim 5, wherein the first end of the transfer tube is located adjacent to said filter means in the lower end of the vial.

7. The vial of claim 3, wherein the transfer tube is integral with the side wall.

8. The vial of claim 4, wherein the transfer tube is integral with the side wall.

9. The vial of claim 5, wherein the transfer tube is integral with the side wall.

10. The vial of claim 6, wherein the transfer tube is integral with the side wall.

11. The vial of claim 1, wherein the fitting for receiving the external air pressure source is centrally located in the closure.

12. A method for using an external pressure source to provide measured aliquots of filtered serum from the piston-type filter/dispenser vial of claim 16 comprising the steps of:
 a. inserting the vial filter end first into a test tube containing a coagulated centrifuged whole blood sample to thereby cause filtered serum to flow up through the filter means into the hollow shaft of the vial;
 b. connecting the external pressure source to the pressure fitting; and
 c. applying a predetermined volume of the air to the inside of the vial from the external pressure source to transfer a predetermined aliquot of filtered serum out of the vial through the transfer tube.

13. The method of claim 12, wherein the external pressure source comprises a pipette.

14. A method for using an external pressure source to provide measured aliquots of filtrate from the filter/dispenser vial of claim 16 comprising the steps of:
 a. inserting the vial filter end first into a test tube containing a solution to be filtered to thereby cause filtrate to flow up through the filter means into the hollow shaft of the vial;
 b. connecting the external pressure source to the pressure fitting; and
 c. applying a predetermined volume of the air to the inside of the vial from the external pressure source to transfer a predetermined aliquot of filtered serum out of the vial through the transfer tube.

15. The method of claim 14, wherein the external pressure source comprises a pipette.

* * * * *